(12) United States Patent
Kim et al.

(10) Patent No.: US 11,040,224 B2
(45) Date of Patent: Jun. 22, 2021

(54) INNER PHASE THICKENED WATER-IN-OIL COSMETIC COMPOSITION

(71) Applicant: AMOREPACIFIC CORPORATION, Seoul (KR)

(72) Inventors: Kyung Nam Kim, Yongin-si (KR); Kyung Ho Choi, Yongin-si (KR); Yeong Jin Choi, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 21 days.

(21) Appl. No.: 16/511,664

(22) Filed: Jul. 15, 2019

(65) Prior Publication Data

US 2019/0336797 A1   Nov. 7, 2019

Related U.S. Application Data

(63) Continuation of application No. 14/344,392, filed as application No. PCT/KR2012/007384 on Sep. 14, 2012, now abandoned.

(30) Foreign Application Priority Data

Sep. 16, 2011 (KR) .......................... 10-2011-0093633

(51) Int. Cl.

| | |
|---|---|
| *A61Q 1/00* | (2006.01) |
| *A61K 8/73* | (2006.01) |
| *A61Q 19/00* | (2006.01) |
| *A61K 8/06* | (2006.01) |
| *A61K 8/91* | (2006.01) |
| *A61K 8/81* | (2006.01) |
| *A61Q 1/02* | (2006.01) |

(52) U.S. Cl.
CPC ................ *A61Q 1/00* (2013.01); *A61K 8/064* (2013.01); *A61K 8/73* (2013.01); *A61K 8/737* (2013.01); *A61K 8/8152* (2013.01); *A61K 8/91* (2013.01); *A61Q 19/00* (2013.01); *A61K 2800/10* (2013.01); *A61K 2800/48* (2013.01); *A61Q 1/02* (2013.01)

(58) Field of Classification Search
CPC ........ A61Q 1/00; A61K 8/737; A61K 8/8152; A61K 2800/48
See application file for complete search history.

(56) References Cited

U.S. PATENT DOCUMENTS

| | | | |
|---|---|---|---|
| 5,254,331 A | 10/1993 | Mausner | |
| 5,855,898 A * | 1/1999 | Baines | ..................... A61K 8/73 424/401 |
| 6,235,297 B1 | 5/2001 | Antonelli et al. | |
| 2013/0130959 A1 | 5/2013 | Li et al. | |

FOREIGN PATENT DOCUMENTS

| | | |
|---|---|---|
| CN | 101808618 A | 8/2010 |
| CN | 102970963 A | 3/2013 |
| KR | 10-1999-0047799 A | 7/1999 |
| KR | 10-2007-0052486 A | 5/2007 |
| KR | 10-2009-0074877 A | 7/2009 |
| KR | 10-2009-0113375 A | 5/2011 |
| KR | 10-2011-0056877 A | 5/2011 |
| WO | 2009/042732 A1 | 4/2009 |

OTHER PUBLICATIONS

Dolz et al. (Journal of Food Engineering 81 (2007) 179-186) (Year: 2007).*
Mallo, P. et al. "Thickening Agent with a High Salt Tolerance" Cosmetic Science Technology 2011, p. 1 (Year: 2011).*
Xinhai (http://www.bombayhouse.Org/service/wc-thf-thickening-agent-manufacturer/8394/#) p. 1-7, accessed Nov. 29, 2017 (Year: 2017).*
International Search Report for International Patent Application No. PCT/KR2012/007384 (dated Feb. 1, 2013).
Chinese Office Action for Chinese Patent Application No. 201280044788.5 (dated Apr. 28, 2015).
Office Action from Chinese Patent Application No. 201280044788.5 (dated Dec. 18, 2015).
Office Action from corresponding Chinese Patent Application No. 201280044788.5 (dated Sep. 19, 2016).
Wang, "Green water purifying ingredient,", Scientific and Technical Documents Publishing House, p. 58 (2006).
Wang, "Functional polymer material", Tongji University Press, p. 343 (2010).
Mallo, P. et al. "Thickening Agent with a High Salt Tolerance" Cosmetic Science Technology 2011, p. 1 (2011).
Mason, D. "Part 12: Emulsions and Their Formation" (http://blog.fqechemicals.com/emulsions-and-their-formation) Aug. 3, 2016, p. 1-9 (2016).
Xinhai (http://www.bombayhouse.org/service/wc-thf-thickening-agent-manufacturer/8394/#) p. 1-7, accessed Nov. 29, 2017 (2017).
Disteardimonium Hectorite (https://www.ewg.org/skindeep/ingredient/702178/DISTEARDIMON IU M_H ECTORITE/) copyright 2007, p. 1-2. (2007).
Polyelectrolytes, (http://infohouse.p2ric.org/ref/10/09949.htm) accessed Jun. 30, 2016, p. 1 (2016).
Butylene Glycol (https://www.ewg.org/skindeep/ingredient/700861/BUTYLEN E_ GLYCOL/) copyright 2007, p. 1-2 (2007).

(Continued)

*Primary Examiner* — Andrew S Rosenthal
(74) *Attorney, Agent, or Firm* — Merchant & Gould P.C.

(57) ABSTRACT

Provided is a water-in-oil cosmetic composition comprising one or more thickening agents selected from the group consisting of sodium polyacrylate starch, polyacrylate crosspolymer-6, xanthan gum and locust bean gum in an inner phase. The water-in-oil cosmetic composition of the present invention brings improvements to time-related changes in preparation stability by means of inner phase thickening controlling the flow properties of an aqueous phase, and controls the size of emulsified particles by means of inner phase thickening, and as a result the invention has outstanding thixotropic characteristics and outstanding initial spreadability and has outstanding durability and, in addition, the invention provides both a fresh-cream-like soft feel in use and a liquid-like light feel in use.

5 Claims, 4 Drawing Sheets

(56) References Cited

OTHER PUBLICATIONS

Sorbitan Isostearate (https://www.ewg.org/skindeep/ingredient/706228/SORBITAN_ISOSTEARATE/) copyright 2007, p. 1-2. (2007).
Lauryl P., "EG-9 Polydi methylsiloxyethyl Di methicone," (https://www.ewg.org/skindeep/ingredient/726466/LAU RYL_P EG-9 _ POLYDIMETHYLSILOXYETHYL_DIMETHICONE/) copyright 2007, p. 1-2. (2007).
Dicaprylyl Carbonate (https://www.ewg.org/skindeep/ingredient/701945/DICAPRYLYL_CARBONATE/) copyright 2007, p. 1-2. (2007).
Sepimax Zen. (http://www.in-cosmeticsasia.com/_novadocuments/39896?v=635169726331670000) accessed Jun. 30, 2016, p. 1-5 (2016).
Phenoxyethanol (https://www.ewg.org/skindeep/ingredient/704811/PHENOXYETHANOL/) copyright 2007, pp. 1-3. (2007).
MSDS (http://www.lotioncrafter.com/reference/sds_sepimax_zen_20120302.pdf), Feb. 3, 2012, p. 1-10 (2012).
Glycerin (https://www.ewg.org/skindeep/ingredient/702620/GLYCERI NI) copyright 2007, p. 1-3. (2007).
Chinese Office Action for Chinese Patent Application No. 201810874324.6 (dated Oct. 16, 2020).
Ryu Chang-Sung et al., "Polymer Chemistry and Polymer Physics Comprehensive Experiment Curriculum", China Geotechnical University Press: 39-40 (2009).
Office Action for Chinese Patent Application No. 2018108743246 (dated Mar. 23, 2021).

* cited by examiner (a)

(b)

Mastersizer Measurement

INNER PHASE THICKENED WATER-IN-OIL COSMETIC COMPOSITION

This application is a Continuation of U.S. application Ser. No. 14/344,392, filed 12 Mar. 2014, which is a U.S. National Stage Application under 35 U.S.C. § 371 of International Patent Application No. PCT/KR2012/007384, filed 14 Sep. 2012, which claims the benefit of priority to Korean Patent Application No. 10-2011-0093633, filed 16 Sep. 2011, the disclosures of all of which are hereby incorporated by reference in their entireties. The International Application was published in Korean on 21 Mar. 2013 as WO 2013/039353.

TECHNICAL FIELD

The present disclosure relates to an inner phase-thickened water in oil type cosmetic composition. More particularly, the present disclosure relates to a water in oil type cosmetic composition including a thickening agent that controls the flowability of an aqueous phase portion and having excellent formulation stability and thixotropic properties.

BACKGROUND ART

In the field of cosmetics, technology of controlling the flowability of a formulation is one of the technologies that has been developed and advanced continuously to date. It is the reason why controlling the flowability of a cosmetic product is important that a cosmetic product has low flowability during the storage before its application, is converted to fluid having high flowability under the friction during its application, and provides various functions as cosmetics while its flowability disappears in the absence of friction. Such a phenomenon including an increase in flowability due to the friction in a cosmetic agent and a drop in flowability due to the extinction of friction is referred to as thixotropy.

In general, when applying a cosmetic agent to the skin, the resistance experienced by the hands and skin is pointed out as a negative factor, such as dryness or stifling feel. Thus, easy spreadability upon skin application has been regarded as one of the important factors determining the quality of a cosmetic product. The above-mentioned thixotropy may be manifested as light spreadability in the case of moisturizing cream or the like, as application uniformity of a pigment expressing skin color and a thin cosmetic film in the case of makeup cosmetics including foundation, and as high UV protecting efficiency derived from application uniformity of a UV protecting ingredient in the case of UV protecting agents.

Water in oil type flow controlling agents that have been developed to date may be classified broadly into inorganic flow controlling agents and organic flow controlling agents. While inorganic flow controlling agents include organic smectite obtained by surface treatment of smectite derived from clay so as to be applied to oil as a continuous phase, organic flow controlling agents include low-melting point wax, dextrin palmitate, trihydroxystearin or the like.

Meanwhile, emulsion formulations may be classified broadly into oil in water cosmetic agents and water in oil cosmetic agents. In the case of oil in water cosmetic agents, the outer phase is formed of water. In the case of water in oil cosmetic agents, the outer phase is formed of an oil phase. In general, thickening is performed merely in the outer phase to control the properties, such as hardness and viscosity, related to the appearance of a formulation. However, there have been little studies about improvement of the properties, stability and feel in use of a formulation based on the thickening of an inner phase of emulsion.

DISCLOSURE

Technical Problem

A technical problem to be solved by the present disclosure is to provide a cosmetic composition having high formulation stability and excellent thixotropic properties and thus showing a liquid-like light feel in use despite its formulation as cream. In the cosmetic composition according to the present disclosure, the aqueous phase as inner phase of a water in oil cosmetic agent is thickened with no use of a dispersant or wax in a water in oil emulsion type makeup formulation, thereby controlling the flowability of aqueous phase. Another technical problem to be solved by the present disclosure is to provide a water in oil emulsion type makeup cosmetic composition which has high stability with time through the inner phase thickening using a thickening agent controlling the flowability of an aqueous phase, and provides a fresh cream-like soft feel in use.

Technical Solution

In one general aspect, there is provided a water in oil type cosmetic composition including, in its inner phase, at least one thickening agent selected from the group consisting of sodium polyacrylate starch, polyacrylate crosspolymer-6, xanthan gum and locust beam gum.

According to an embodiment, the thickening agent may be at least one of sodium polyacrylate starch and polyacrylate crosspolymer-6.

According to another embodiment, the thickening agent may be used in an amount of 0.01-5.0 wt % based on the total weight of the composition.

According to still another embodiment, the composition may have thixotropy.

According to yet another embodiment, the composition may be a makeup cosmetic composition.

Advantageous Effects

According to the embodiments of the present disclosure, the water in oil type cosmetic composition uses inner phase thickening controlling the flowability of an aqueous phase to improve variations in formulation stability with time and to control the size of emulsion particles, thereby providing excellent thixotropic properties and initial spreadability, high durability, a fresh cream-like soft feel in use and a liquid-like light feel in use.

BEST MODE

Hereinafter, exemplary embodiments now will be described more detail to provide the present disclosure fully understood to carry out by those skilled in the art.

In an aspect, there is provided a cosmetic composition. The cosmetic composition is a water in oil type cosmetic composition including an outer phase and an inner phase, wherein the inner phase includes at least one thickening agent selected from the group consisting of sodium polyacrylate starch, polyacrylate crosspolymer-6, xanthan gum and locust bean gum.

The water in oil type emulsion makeup cosmetic composition according to the present disclosure uses inner phase thickening to control the flowability of an aqueous phase. It is shown that such inner phase thickening minimizes variations in formulation stability with time.

Water-soluble thickening agents may be classified into inorganic thickening agents including inorganic metal oxides and organic thickening agents including water-soluble polymer materials. According to an embodiment, water-soluble inorganic thickening agents having great possibility of skin allergy are not used but water-soluble organic thickening agents of polysaccharides are used.

Figure 1:
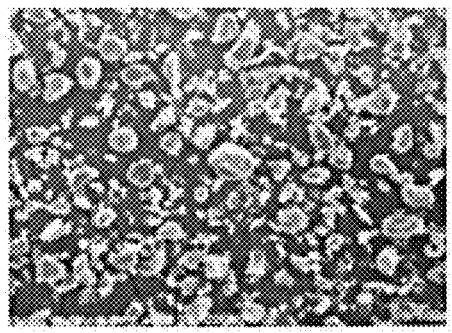
FIG. 1 is an SEM (scanning electron microscopy) image (a) and particle size distribution graph (b) of sodium polyacrylate starch contained in the cosmetic composition according to an embodiment of the present disclosure.
Figure 1:
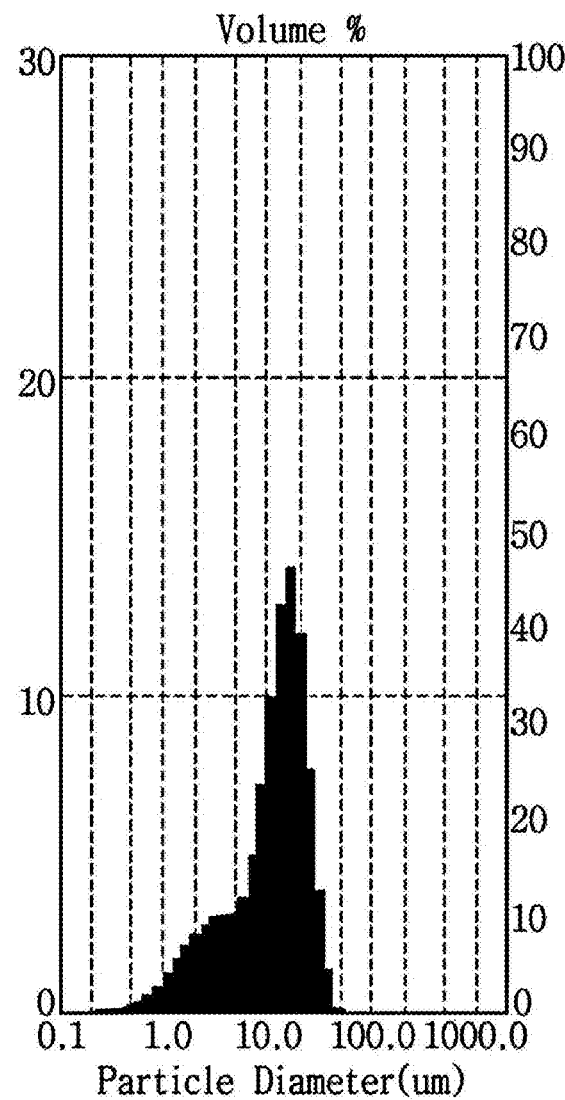

The thickening agent may be at least one selected from the group consisting of sodium polyacrylate starch, polyacrylate crosspolymer-6, xanthan gum and locust bean gum. More preferably, the thickening agent may be at least one of sodium polyacrylate starch and polyacrylate crosspolymer-6. Most preferably, the thickening agent may be sodium polyacrylate starch. However, any thickening agent may be used with no particular limitation, as long as it causes an increase in viscosity. FIG. 1 shows an SEM image (a) and particle size distribution graph (b) of sodium polyacrylate starch. After determining the average particle size of sodium polyacrylate starch by Mastersizer, it is 12 μm.

The thickening agent may be used in an amount of 0.01-5.0 wt % based on the total weight of the composition. More preferably, it may be used in an amount of 0.05-1.0 wt %. When the thickening agent is used in an amount less than 0.01 wt %, it is not possible to obtain a sufficient thickening effect. When the thickening agent is used in an amount greater than 5.0 wt %, the viscosity of aqueous phase increases excessively, and thus the composition takes the form of hard solid gel, has high stickiness and does not provide properties as a makeup cosmetic composition any longer. Moreover, in the latter case, the composition undergoes pigment agglomeration upon emulsification and has poor stability due to its unstable emulsion state.

The composition according to the present disclosure has thixotropy. Thixotropic properties, also called thixotropy, are referred to as properties including an increase in flowability caused by friction and a drop in flowability upon extinction of friction. By virtue of such thixotropy, the composition according to the present disclosure shows increased flowability upon friction against the skin when applying it to the skin, and is spread on the skin softly and smoothly, thereby providing excellent spreadability and feel in use. After the skin application, the composition according to the present disclosure has decreased flowability, thereby providing excellent durability. Particularly, the composition according to the present disclosure does not use a dispersant and wax but is based on inner phase thickening to control the flowability. Thus, the composition according to the present disclosure is produced in a simple manner, and has a light feel in use and high durability.

Pigments used in water in oil emulsion may be classified into water-based dispersion pigments and oil-based dispersion pigments, depending on dispersed phases of pigments. In general, in the case of water in oil emulsion, a pigment coated with alkylsilane or dimethicone is dispersed into an oil-based outer phase. In this case, the pigment is positioned at the outer part of emulsion, and thus is more stable as compared to the dispersion into a water-based inner phase. However, when the pigment is dispersed into the water-based inner phase rather than oil-based outer phase, it is possible to carry out dispersion of pigment in a greater amount more homogeneously. In fact, it has been reported that oil phase dispersion causes significant filling-up and aqueous phase (inner phase) dispersion improves such filling-up.

Therefore, according to the present disclosure, the pigment is dispersed into an aqueous phase. Although there is no particular limitation in pigments for this purpose, a silica-coated pigment is used preferably. The surface of pigment is provided with hydrophilic properties by virtue of such silica coating, thereby ensuring dispersibility.

There is no particular limitation in the formulation of cosmetic composition according to the present disclosure, and any formulation may be selected suitably as desired. For example, the cosmetic composition may be provided as at least one formulation selected from the group consisting of skin lotion, skin softener, skin toner, astringent, lotion, milk lotion, moisture lotion, nourishing lotion, massage cream, nourishing cream, moisture cream, hand cream, foundation, makeup base, primer, essence, nourishing essence, pack, soap, cleansing foam, cleansing lotion, cleansing cream, body lotion and body cleanser. Preferably, the formulation is foundation, makeup base or primer, but is not limited thereto.

When the cosmetic composition is provided as a formulation of paste, cream or gel, animal fibers, vegetable fibers, wax, paraffin, starch, tragacanth, cellulose derivatives, polyethylene glycol, silicone, bentonite, silica, talk or zinc oxide may be used as a carrier ingredient.

When the cosmetic composition is provided as a formulation of powder or spray, lactose, talc, silica, aluminum hydroxide, calcium silicate or polyamide powder may be used as a carrier ingredient. Particularly, in the case of spray, a propellant, such as chlorofluorohydrocarbon, propane/butane or dimethyl ether, may be further used.

When the cosmetic composition is provided as a formulation of solution or emulsion, a solvent, solvating agent or emulsifier may be used as a carrier ingredient, and particular examples thereof include water, ethanol, isopropanol, ethyl carbonate, ethyl acetate, benzyl alcohol, benzyl benzoate, propylene glycol, 1,3-butylene glycol oil, glycerol fatty ester, polyethylene glycol or sorbitan fatty acid ester.

When the cosmetic composition is provided as a formulation of suspension, a liquid diluent such as water, ethanol or propylene glycol, a suspending agent such as ethoxylated isostearyl alcohol, polyoxyethylene sorbitol ester or polyoxyethylene sorbitan ester, microcrystalline cellulose, aluminum meta-hydroxide, bentonite, agar, tragacanth or the like may be used.

When the cosmetic composition is provided a formulation of surfactant-containing cleanser, aliphatic alcohol sulfate, aliphatic alcohol ether sulfate, sulfosuccinic acid monoester, isethionate, imidazolinium derivative, methyl taurate, sarcosinate, fatty acid amide ether sulfate, alkylamidobetain, aliphatic alcohol, fatty acid glyceride, fatty acid diethanol amide, vegetable oil, linoline derivative or ethoxylated glycerol fatty acid ester or the like may be used as a carrier ingredient.

The cosmetic composition may further include functional additives and other ingredients used in conventional cosmetic compositions. Such functional additives include any ingredients selected from the group consisting of water-soluble vitamins, oil-soluble vitamins, polymeric peptides, polysaccharides, spingolipids and seaweed extract.

The cosmetic composition may be formulated by using any desired ingredients used in conventional cosmetic compositions in addition to such functional additives. Such ingredients may include fat and oil ingredients, moisturizing agents, emollients, surfactants, organic and inorganic pigments, organic powder, UV absorbing agents, preservatives, sterilizing agents, antioxidants, plant extract, pH modifiers, alcohols, colorants, fragrant, blood circulation accelerators, coolants, antiperspirants, purified water or the like.

The present disclosure now will be described in more detail hereinafter with reference to Examples. However, the present disclosure may be embodied in many different forms and should not be construed as limited to the exemplary embodiments set forth therein.

Examples 1-4 and Comparative Example 1

Water in oil emulsion formulations of Comparative Example 1 and Examples 1-4 are obtained by using the formulations as shown in Table 1 in the conventional manner. Comparative Example 1 is the control using no aqueous phase thickening agent, and Examples 1-4 are obtained by using an aqueous phase thickening agent.

TABLE 1

| Item | Ingredients | Comp. Ex. 1 | Ex. 1 | Ex. 2 | Ex. 3 | Ex. 4 |
| --- | --- | --- | --- | --- | --- | --- |
| Emulsifier | LaurylPEG-9 polydimethylsiloxyethyl dimethicone | 3.0 | 3.0 | 3.0 | 3.0 | 3.0 |
| | Sorbitan isostearate | 1.0 | 1.0 | 1.0 | 1.0 | 1.0 |
| Oil phase ingredients | Decamethylcyclopenta siloxane | 20.0 | 20.0 | 20.0 | 20.0 | 20.0 |
| | Dicaprylyl carbonate | 10.00 | 10.00 | 10.00 | 10.00 | 10.00 |
| | Squalane | 10.00 | 10.00 | 10.00 | 10.00 | 10.00 |
| Oil phase thickening agent | Distearmonium hectorite | 1.0 | 1.0 | 1.0 | 1.0 | 1.0 |
| Aqueous phase ingredients | Purified water | To 100 | To 100 | To 100 | To 100 | To 100 |
| | Butylene glycol | 4.0 | 4.0 | 4.0 | 4.0 | 4.0 |
| | Glycerin | 4.0 | 4.0 | 4.0 | 4.0 | 4.0 |
| | Phenoxyethanol | 0.3 | 0.3 | 0.3 | 0.3 | 0.3 |
| Aqueous phase thickening agent | Xanthan gum | — | 0.5 | — | — | — |
| | Locust bean gum | — | — | 0.5 | — | — |
| | Polyacrylate crosspolymer-6 | — | — | — | 0.5 | — |
| | Sodium polyacrylate starch | — | — | — | — | 0.5 |

[Test Example 1] Test for Determining Stability Depending on Aqueous Phase Thickening Agent The emulsion stability and variations in hardness with time are evaluated depending on the particular type of water-soluble thickening agent by using Examples 1-4 and Comparative Example 1.

Evaluation of emulsion stability is carried out by measuring the stability for 1 week in a shaking incubator capable of temperature control. One temperature cycle includes −10° C., 30° C. and 45° C. each for 8 hours. Emulsion stability is determined for 7 days in 1 cycle per day by observing occurrence of oil separation, band formation, precipitation, etc. For all samples, data are acquired five times to obtain results. When a sample shows no abnormality for 5 times, it is expressed by ○. When a sample shows abnormality for 1~2 times, it is expressed by Δ. When a sample shows abnormality for 3 times or more, it is expressed by X. Pigment dispersibility is determined by a dispersion degree of pigment in an aqueous phase, and evaluated according to the same criteria as the emulsion stability.

Variations in hardness with time are determined by measuring the hardness of a sample by Rheometer (CR-500DX, Sun Scientific), after the prepared sample is stored in a constant-temperature bath at 30° C. Hardness is compared between the sample after preparation and the sample after 1 week to determine the stability. The results are shown in Table 2.

TABLE 2

| | Comp. Ex. 1 1 | Ex. 1 2 | Ex. 2 3 | Ex. 3 4 | Ex. 4 5 |
| --- | --- | --- | --- | --- | --- |
| Emulsion stability | X | Δ | Δ | ○ | ○ |
| Variations in hardness with time | −28% | −15% | −8% | +9.5% | +13.6% |

As can be seen from Table 2, only Comparative 1 using no aqueous phase thickening shows poor stability. Examples 1-4 substantially maintain their stabilities. In addition, as compared to Examples 1 and 2 (xanthan gum, locust bean gum), thickening in Examples 3 and 4 (sodium polyacrylate starch, polyacrylate crosspolymer-6) provides higher stability. In terms of variations in hardness with time, Examples 3 and 4 maintain their most stable states with no drop in hardness.

[Test Example 2] Images Taken by Electron Microscope

Comparative Example 1, and Examples 3 and 4 are imaged by electron microscopy. The results of Comparative Example 1, Example 3 and Example 4 are shown in FIG. 3, FIG. 4 and FIG. 5, respectively.

Figure 3:
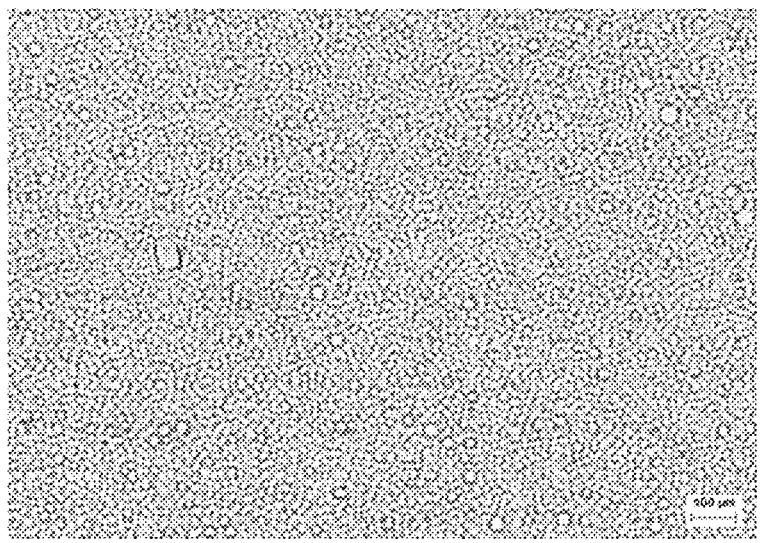
FIG. 3 to FIG. 5 are electron microscopy images of the cosmetic composition according to an embodiment of the present disclosure.
Figure 4:
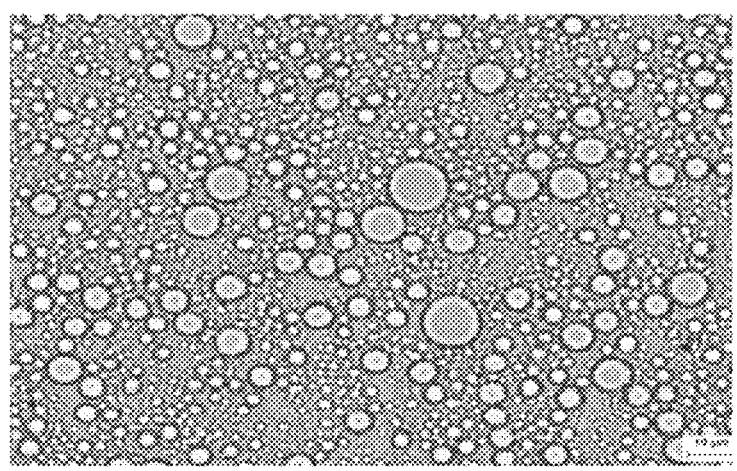
Figure 5:
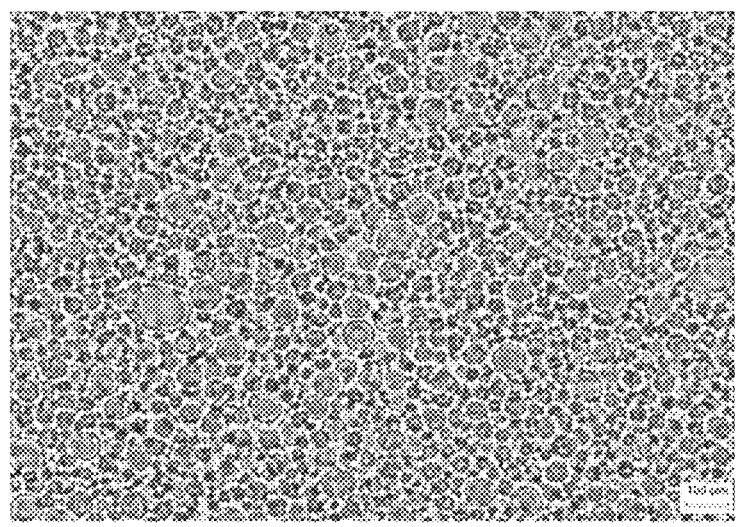

As can be seen from FIG. 3 to FIG. 5, the emulsion particles of Example 4 form a bi-modal condition and realize a feel in use caused by easy collapse of the particles.

[Preparation Example] Preparation of Foundation

A pigment is added to each of Comparative Example 1 and Example 4 (according to the composition as shown in Table 3) to obtain water in oil emulsion foundation in the conventional manner. Comparative Example 1 is the control using no aqueous phase thickening agent. Example 4 having high emulsion stability and showing the lowest variation in hardness with time is used.

TABLE 3

| Item | Ingredient | Comp. Ex. 1 | Ex. 4 |
| --- | --- | --- | --- |
| Emulsifier | LaurylPEG-9 polydimethylsiloxyethyl-dimethicone | 3.0 | 3.0 |
|  | Sorbitan isostearate | 1.0 | 1.0 |
| Oil phase ingredients | Decamethylcyclopentasiloxane | 20.0 | 20.0 |
|  | Dicaprylyl carbonate | 10.00 | 10.00 |
|  | Squalane | 10.00 | 10.00 |
| Oil phase thickening agent | Distearmonium hectorite | 1.0 | 1.0 |
| Pigment | Oil phase pigment | 10.0 | 10.0 |
| Aqueous phase ingredients | Purified water | To 100 | To 100 |
|  | Butylene glycol | 4.0 | 4.0 |
|  | Glycerin | 4.0 | 4.0 |
|  | Phenoxyethanol | 0.3 | 0.3 |
| Aqueous phase thickening agent | Sodium Polyacrylate starch | — | 0.5 |

[Test Example 3] Test for Determining Thixotropy, Easy Spreadability and Uniform Applicability The foundation obtained from the above Preparation Example is observed in terms of its thixotropy, easy spreadability and uniform applicability. The thixotropy is determined by RHEOMETER AR2000 (TA Instruments, England) and the results are shown in Table 4 and FIG. 2. Easy spreadability and uniform applicability are determined based on the test scores from professional panels by taking score 5 as the highest score. The results are shown in Table 4.

TABLE 4

| Item | Thixotropy | Easy spreadability | Uniform Applicability |
| --- | --- | --- | --- |
| Comp. Ex. 1 | poor | 3.1 | 2.8 |
| Ex. 4 | High | 4.8 | 4.6 |

Figure 2:
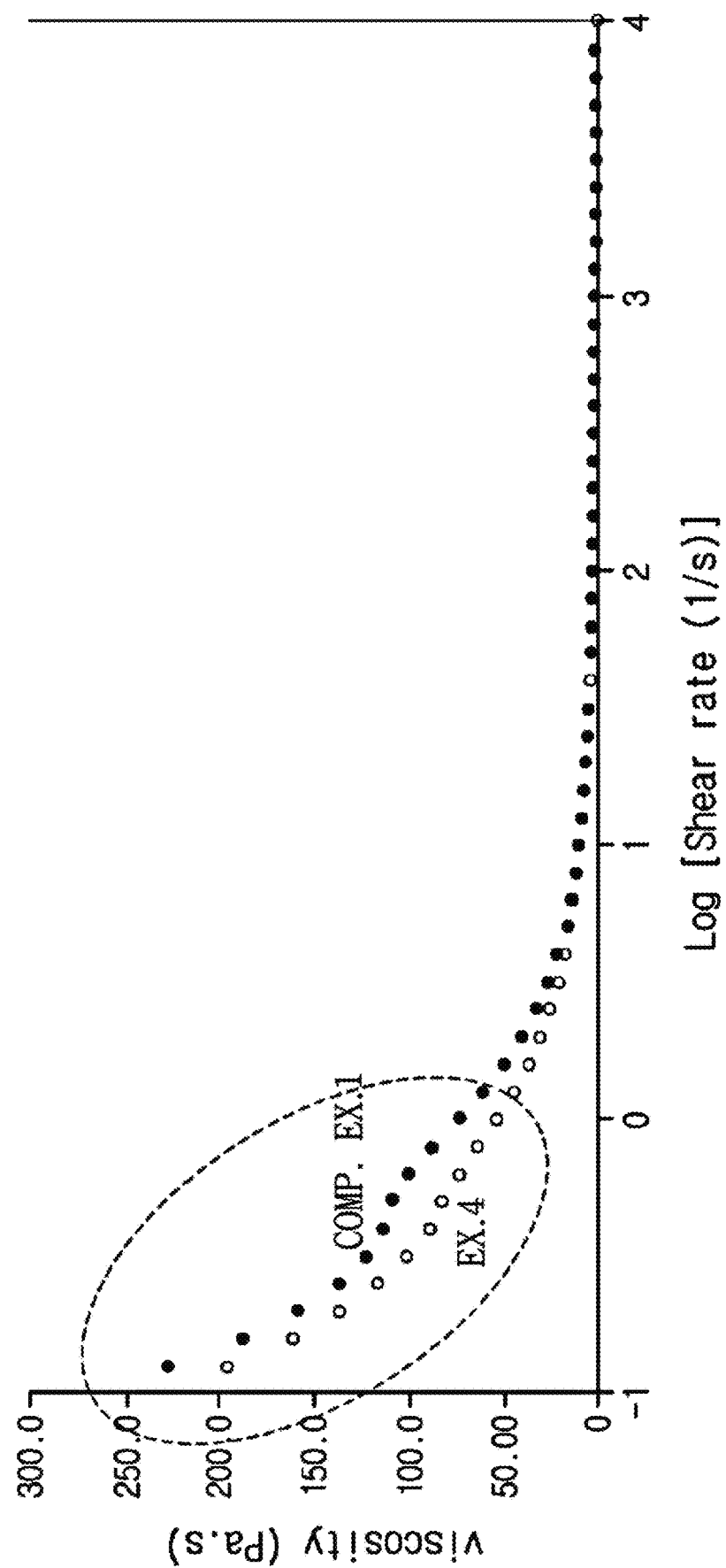
FIG. 2 is a graph illustrating the thixotropic properties of the cosmetic composition according to an embodiment of the present disclosure.

As can be seen from Table 4 and FIG. 2, the foundation using Example 4 provides higher thixotropy, easy spreadability and uniform applicability as compared to the foundation using Comparative Example 1.

We claim:

1. A method for enhancing thixotropy of a cosmetic composition when applying the cosmetic composition onto a skin comprising adding at least one thickening agent selected from the group consisting of sodium polyacrylate starch and polyacrylate crosspolymer-6 to the cosmetic composition, wherein the cosmetic composition is a water in oil type cosmetic composition, and the thickening agent is added to an aqueous phase as an inner phase of the cosmetic composition.

2. The method according to claim 1, wherein the thickening agent is used in an amount of 0.01-5.0 wt % based on the total weight of the composition.

3. The method according to claim 1, wherein the composition is a makeup cosmetic composition.

4. The method according to claim 1, wherein the composition does not include a dispersant or a wax.

5. The method according to claim 1, wherein thixotropy is determined by a rheometer.

* * * * *